(12) United States Patent
Johnson et al.

(10) Patent No.: US 10,450,574 B2
(45) Date of Patent: Oct. 22, 2019

(54) TRANSIENT TRANSFECTION METHOD FOR RETROVIRAL PRODUCTION

(71) Applicant: GLAXOSMITHKLINE INTELLECTUAL PROPERTY DEVELOPMENT LIMITED, Brentford (GB)

(72) Inventors: Sabine Johnson, Stevenage (GB); Celeste Pallant, Stevenage (GB); Eirini Vamva, Stevenage (GB); Conrad Vink, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 15/356,813

(22) Filed: Nov. 21, 2016

(65) Prior Publication Data
US 2017/0145427 A1    May 25, 2017

(30) Foreign Application Priority Data

Nov. 24, 2015 (GB) .................................. 1520764.0
May 26, 2016 (GB) .................................. 1609354.4

(51) Int. Cl.
| C12Q 1/68 | (2018.01) |
| A61K 39/21 | (2006.01) |
| C12N 15/03 | (2006.01) |
| C12N 15/87 | (2006.01) |
| C12N 15/867 | (2006.01) |
| C12N 15/64 | (2006.01) |
| C12N 7/00 | (2006.01) |
| C12N 15/85 | (2006.01) |
| C12N 15/86 | (2006.01) |
| C12N 15/67 | (2006.01) |
| C12N 15/88 | (2006.01) |
| C12N 15/89 | (2006.01) |

(52) U.S. Cl.
CPC .............. *C12N 15/64* (2013.01); *C12N 7/00* (2013.01); *C12N 15/67* (2013.01); *C12N 15/85* (2013.01); *C12N 15/86* (2013.01); *C12N 15/88* (2013.01); *C12N 15/895* (2013.01); *C12N 2740/16043* (2013.01); *C12N 2740/16052* (2013.01); *C12N 2800/204* (2013.01); *C12N 2800/22* (2013.01); *C12N 2800/50* (2013.01)

(58) Field of Classification Search
None
See application file for complete search history.

(56) References Cited

U.S. PATENT DOCUMENTS

| 6,677,155 B1 | 1/2004 | Sena-Esteves et al. |
| 2006/0057553 A1 | 3/2006 | Aguilar-Cordova |
| 2010/0003746 A1* | 1/2010 | Lesch ................ A61K 48/0091 435/320.1 |
| 2012/0121650 A1 | 5/2012 | Johnston et al. |
| 2012/0142049 A1 | 6/2012 | Belmont et al. |
| 2015/0191745 A1 | 7/2015 | Charneau et al. |
| 2017/0145388 A1 | 5/2017 | Johnson et al. |
| 2017/0175136 A1* | 6/2017 | Stamatoyannopoulos ................. C12N 15/86 |

FOREIGN PATENT DOCUMENTS

| AU | 2013205006 A1 | 4/2013 |
| EP | 1652932 A1 | 5/2006 |
| EP | 1743942 A1 | 1/2007 |
| GB | 2538321 A | 11/2016 |
| GB | 2538324 A | 11/2016 |
| WO | WO1995003400 | 2/1995 |
| WO | WO1997030169 | 8/1997 |
| WO | WO99/43842 | 9/1999 |
| WO | WO 00/39303 A2 | 7/2000 |
| WO | WO2000065077 | 11/2000 |
| WO | WO2000066758 | 11/2000 |
| WO | WO2000075299 | 12/2000 |
| WO | WO 01/91802 A1 | 12/2001 |
| WO | WO 02/22663 A2 | 3/2002 |
| WO | WO02/053576 | 7/2002 |
| WO | 2002072836 A2 | 9/2002 |
| WO | WO 03/064665 A2 | 8/2003 |
| WO | WO03/087330 | 10/2003 |
| WO | WO 2006/058231 A2 | 6/2006 |
| WO | WO2008/099148 | 8/2008 |
| WO | WO2009/146150 | 12/2009 |
| WO | WO 2012/028681 A1 | 3/2012 |
| WO | WO 2012/170431 A2 | 12/2012 |
| WO | 2013121194 A1 | 8/2013 |

OTHER PUBLICATIONS

Shizuya, et al., *Keio J. Med.*, 50(1):26-30 (2001).
Lesch, Generation of lentivirus vectors using recombinant baculoviruses et al., *Gene Therapy*, 15:1280-1286 (2008).
Maria Mercedes Segura et al.: "New Developments in Lentiviral Vector Design, Production and Purification", Expert Opinion on Bioological Therapy, vol. 13, No. 7, Apr. 16, 2013 (Apr. 16, 2013), pp. 987-1011, XP055340869, Ashley, London; GB ISSN: 1471-2598, DOI: 10.1517/14712598.2013/79249 cited in the application, figure 1.
Ni et al., Generation of a packaging cell line for prolonged large-scale production of high-titer HIV-1-based lentiviral vector, J Gene Med.,7(6):818-34 (2005).

(Continued)

*Primary Examiner* — Maria Marvich
(74) *Attorney, Agent, or Firm* — James J. Kang; Duke M. Fitch (57) ABSTRACT

The invention relates to bacterial artificial chromosomes (BAC) comprising retroviral nucleic acid sequences encoding: gag and pol proteins, and an env protein or a functional substitute thereof, wherein each of the retroviral nucleic acid sequences are arranged as individual expression constructs within the BAC. The invention also relates to uses and methods of transient transfection using said BAC.

24 Claims, 3 Drawing Sheets

(56) References Cited

OTHER PUBLICATIONS

Niebert et al., Characterization of chromosomally assigned replication-competent gamma porcine endogenous retroviruses derived from a large white pig and expression in human cells, J Virol., 76(6):2714-20 (2002).

Recillas-Targa, Multiple strategies for gene transfer, expression, knockdown, and chromatin influence in mammalian cell lines and transgenic animals, Mol Biotechnol., 34(3):337-54 (2006).

Sanber, Khaled S., et al., "Construction of stable packaging cell lines for clinical lentiviral vector production", Scientific Reports, vol. 5, No. 1, (XP055491335 (2015)).

* cited by examiner

FIGURE 3

TRANSIENT TRANSFECTION METHOD FOR RETROVIRAL PRODUCTION

CROSS REFERENCE TO RELATED APPLICATIONS

This application claims the benefit of U.K. Provisional Application No. GB 1520764.0, filed 24 Nov. 2015 and GB 1609354.4, filed 26 May 2016.

FIELD OF THE INVENTION

The invention relates to nucleic acid vectors, in particular bacterial artificial chromosomes, comprising genes required for retroviral production and uses thereof. Also provided are methods of producing replication defective retroviral vector particles comprising the nucleic acid vectors as described herein.

BACKGROUND TO THE INVENTION

In gene therapy, genetic material is delivered to endogenous cells in a subject in need of treatment. The genetic material may introduce novel genes to the subject, or introduce additional copies of pre-existing genes, or introduce different alleles or variants of genes that are present in the subject. Viral vector systems have been proposed as an effective gene delivery method for use in gene therapy (Verma and Somia (1997) *Nature* 389: 239-242).

In particular, these viral vectors are based on members of the retrovirus family due to their ability to integrate their genetic payload into the host's genome. Retroviral vectors are designed to keep the essential proteins required for packaging and delivery of the retroviral genome, but any non-essential accessory proteins including those responsible for their disease profile are removed. Examples of retroviral vectors include lentiviral vectors, such as those based upon Human Immunodeficiency Virus Type 1 (HIV-1), which are widely used because they are able to integrate into non-proliferating cells.

Currently, the majority of viral vectors are produced by transient co-transfection of viral genes into a host cell line. The viral genes are introduced using bacterial plasmids which exist in the host cell for only a limited period of time because the viral genes remain on the plasmids and are not integrated into the genome. As such, transiently transfected genetic material is not passed on to subsequent generations during cell division.

However, there have been several problems associated with the methods of transient transfection currently used, such as batch-to-batch variability, the high cost of transfection reagents and the difficulty to maintain quality control (see Segura et al. (2013) *Expert Opin. Biol. Ther.* 13(7): 987-1011). The process of transfection itself is also labour-intensive and challenging to scale up. There is also the difficult task of removing plasmid impurities which are carried over during vector preparation (see Pichlmair et al. (2007) *J. Virol.* 81(2): 539-47).

It is therefore an object of the present invention to provide an improved method of transient transfection which overcomes one or more of the disadvantages associated with existing methods.

SUMMARY OF THE INVENTION

The present inventors have developed a new way of producing retroviral vectors which involves the use of nucleic acid vectors comprising a non-mammalian origin of replication and the ability to hold at least 25 kilobases (kb) of DNA, such as bacterial artificial chromosomes, comprising all of the retroviral genes essential for retroviral vector production. Current methods of transient transfection require the use of 3-4 separate plasmids carrying different components required for retroviral production to be introduced into the host cell which is time consuming and causes problems associated with selection pressure. The method proposed by the present inventors incorporates all of the essential retroviral genes on a single construct which can then be introduced into a host cell which reduces the amount of material required to transduce the host cell for viral vector production. Therefore, this reduces the cost of goods because only a single vector is used, rather than previous methods which use multiple plasmid vectors.

The use of a nucleic acid vector comprising a non-mammalian origin of replication and which has the ability to hold at least 25 kb of DNA (i.e. large-construct DNA) has several advantages. In the first instance, the vectors can first be manipulated in non-mammalian cells (e.g. microbial cells, such as bacterial cells) rather than mammalian host cells which makes them much easier to use (e.g. bacterial artificial chromosomes can first be manipulated in *E. coli*). Once the nucleic acid vector has been prepared, it can be introduced into a host cell, such as a mammalian host cell, for retroviral vector production.

The use of nucleic acid vectors of the present invention therefore provides advantages in the generation of retroviral vectors.

Therefore, according to a first aspect of the invention, there is provided a bacterial artificial chromosome (BAC), characterized in that said BAC comprises retroviral nucleic acid sequences encoding:

gag and pol proteins, and an env protein or a functional substitute thereof wherein each of the retroviral nucleic acid sequences are arranged as individual expression constructs within the BAC.

According to a further aspect of the invention, there is provided the BAC defined herein for use in a method of producing retroviral vector particles.

According to a further aspect of the invention, there is provided a method of producing a replication defective retroviral vector particle, comprising:

(a) introducing the BAC as defined herein into a culture of mammalian host cells; and (b) culturing the mammalian host cells under conditions in which the replication defective retroviral vector particle is produced.

According to a further aspect of the invention, there is provided a replication defective retroviral vector particle obtained by the method as defined herein.

BRIEF DESCRIPTION OF THE FIGURES

FIG. 2: Comparison of viral titres obtained in Example 2. $10^6$ HEK293T cells were seeded in a 6 well plate. The following day, the adhered cells were transfected using PEI to manufacturer's instruction. Cells were either transfected with a total 4 µg of Wild Type (WT) lentiviral packaging constructs consisting of pMDL.gp (GagPol), pMD.G (VSVg), pK-Rev (Rev) and pCCL.277 (GFP Transfer vector) or 2 μg BACpack (a single BAC construct containing GagPol, VSVg and Rev) plus 2 μg of the eGFP transfer vector on a separate plasmid.

48 hours post transfection, the supernatant was harvested, filtered through a 0.22 μm filter and stored at −80° C. for a minimum of 4 hours. HEK293T cells were seeded for transduction at $10^5$ cells per well in a 24 well plate. The following day viral supernatant was applied to the cells in serial dilutions with Polybrene at a final concentration of 8 μg/ml. 3 days post transduction the cells were harvested by trypsin treatment and analysed for GFP by FACS. Viral titre was calculated as Transduction Units (TU)/mL using the following equation:

$$(GFP\ \text{positive cells}/100) \times \text{dilution factor} \times \text{number of cells transduced}.$$

Viral titres are compared on the bar chart. All incubations were carried out at 37° C. and 5% $CO_2$. Media used was DMEM supplemented with FBS to 10% and 1 μg/ml Doxycycline in the BACpack+Transfer sample.

FIG. 3: Transient Transfection of the BACpack in Adherent HEK293T cells. HEK293T cells transiently transfected with BACpackWTGP-277deIU5, BACpackSYN-277deIU5 or the standard 4 plasmid system using the Calcium Phosphate method. 16 hours post transfection, the +Dox conditions were induced for 24 hours with 1 μg/ml doxycycline. Viral supernatant was harvested 48 post transfection, filtered through a 0.22 μm filter and titrated by transducing HEK293T cells. GFP positive transduced cells were used to calculate the Transducing Units/ml (TU/ml).

DETAILED DESCRIPTION OF THE INVENTION

Definitions

Unless defined otherwise, all technical and scientific terms used herein have the same meaning as is commonly understood by one of skill in the art to which this invention belongs. All patents and publications referred to herein are incorporated by reference in their entirety.

The term "comprising" encompasses "including" or "consisting" e.g. a composition "comprising" X may consist exclusively of X or may include something additional e.g. X+Y.

The term "consisting essentially of" limits the scope of the feature to the specified materials or steps and those that do not materially affect the basic characteristic(s) of the claimed feature.

The term "consisting of" excludes the presence of any additional component(s).

The term "about" in relation to a numerical value x means, for example, x±10%, 5%, 2% or 1%.

The term "vector" or "nucleic acid vector" refers to a vehicle which is able to artificially carry foreign (i.e. exogenous) genetic material into another cell, where it can be replicated and/or expressed. Examples of vectors include non-mammalian nucleic acid vectors, such as bacterial artificial chromosomes (BACs), yeast artificial chromosomes (YACs), P1-derived artificial chromosomes (PACs), cosmids or fosmids.

Other examples of vectors include viral vectors, such as retroviral and lentiviral vectors, which are of particular interest in the present application. Lentiviral vectors, such as those based upon Human Immunodeficiency Virus Type 1 (HIV-1) are widely used as they are able to integrate into non-proliferating cells. Viral vectors can be made replication defective by splitting the viral genome into separate parts, e.g., by placing on separate plasmids. For example, the so-called first generation of lentiviral vectors, developed by the Salk Institute for Biological Studies, was built as a three-plasmid expression system consisting of a packaging expression cassette, the envelope expression cassette and the vector expression cassette. The "packaging plasmid" contains the entire gag-pol sequences, the regulatory (tat and rev) and the accessory (vif, vpr, vpu, net) sequences. The "envelope plasmid" holds the Vesicular stomatitis virus glycoprotein (VSVg) in substitution for the native HIV-1 envelope protein, under the control of a cytomegalovirus (CMV) promoter. The third plasmid (the "transfer plasmid") carries the Long Terminal Repeats (LTRs), encapsulation sequence (ψ), the Rev Response Element (RRE) sequence and the CMV promoter to express the transgene inside the host cell.

The second lentiviral vector generation was characterized by the deletion of the virulence sequences vpr, vif, vpu and nef. The packaging vector was reduced to gag, pol, tat and rev genes, therefore increasing the safety of the system.

To improve the lentiviral system, the third-generation vectors have been designed by removing the tat gene from the packaging construct and inactivating the LTR from the vector cassette, therefore reducing problems related to insertional mutagenesis effects.

The various lentivirus generations are described in the following references: First generation: Naldini et al. (1996) *Science* 272(5259): 263-7; Second generation: Zufferey et al. (1997) *Nat. Biotechnol.* 15(9): 871-5; Third generation: Dull et al. (1998) *J. Virol.* 72(11): 8463-7, all of which are incorporated herein by reference in their entirety. A review on the development of lentiviral vectors can be found in Sakuma et al. (2012) *Biochem. J.* 443(3): 603-18 and Picanco-Castro et al. (2008) *Exp. Opin. Therap. Patents* 18(5):525-539.

The term "non-mammalian origin of replication" refers to a nucleic acid sequence where replication is initiated and which is derived from a non-mammalian source. This enables the nucleic acid vectors of the invention to stably replicate and segregate alongside endogenous chromosomes in a suitable host cell (e.g. a microbial cell, such as a bacterial or yeast cell) so that it is transmittable to host cell progeny, except when the host cell is a mammalian host cell. In mammalian host cells, nucleic acid vectors with non-mammalian origins of replication will either integrate into the endogenous chromosomes of the mammalian host cell or be lost upon mammalian host cell replication. For example, nucleic acid vectors with non-mammalian origins of replication such as bacterial artificial chromosomes (BAC), P1-derived artificial chromosome (PAC), cosmids or fosmids, are able to stably replicate and segregate alongside endogenous chromosomes in bacterial cells (such as *E. coli*), however if they are introduced into mammalian host cells, the BAC, PAC, cosmid or fosmid will either integrate or be lost upon mammalian host cell replication. Yeast artificial chromosomes (YAC) are able to stably replicate and segregate alongside endogenous chromosomes in yeast cells, however if they are introduced into mammalian host cells, the YAC will either integrate or be lost upon mammalian host cell replication. Therefore, in this context, the nucleic acid vectors of the invention act as reservoirs of DNA (i.e. for the genes essential for retroviral production) which can be easily transferred into mammalian cells to generate retroviral vector particles. Examples of non-mammalian origins of replication include: bacterial origins of replications, such as oriC, oriV or oriS; viral origins of replication, such as SV40 origin of replication; or yeast origins of replication, also known as Autonomously Replicating Sequences (ARS elements).

The nucleic acid vectors of the present invention comprise a non-mammalian origin of replication and are able to hold at least 25 kilobases (kb) of DNA. In one embodiment, the nucleic acid vector has the ability to hold at least 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340 or 350 kb of DNA. It will be understood that references to "ability to hold" has its usual meaning and implies that the upper limit for the size of insert for the nucleic acid vector is not less than the claimed size (i.e. not less than 25 kb of DNA).

The aim of the present invention is to include the genes essential for retroviral packaging in a single construct (i.e. the nucleic acid vector). Therefore, the nucleic acid vectors of the invention, must be able to hold large inserts of DNA. For the avoidance of doubt, it will be understood that references to "nucleic acid vectors" or "artificial chromosomes" do not refer to natural bacterial plasmids (e.g. such as the plasmids currently used in transient transfection methods) because these are not able to hold at least 25 kb of DNA. The maximum size insert which a plasmid can contain is about 15 kb. Such nucleic acid vectors also do not refer to bacteriophages which generally only hold maximum inserts of 5-11 kb. Therefore, in one embodiment the nucleic acid vector of the invention is not a plasmid, bacteriophage or episome.

The term "endogenous chromosomes" refers to genomic chromosomes found in the host cell prior to generation or introduction of an exogenous nucleic acid vector, such as a bacterial artificial chromosome.

The terms "transfection", "transformation" and "transduction" as used herein, may be used to describe the insertion of the non-mammalian or viral vector into a target cell. Insertion of a vector is usually called transformation for bacterial cells and transfection for eukaryotic cells, although insertion of a viral vector may also be called transduction. The skilled person will be aware of the different non-viral transfection methods commonly used, which include, but are not limited to, the use of physical methods (e.g. electroporation, cell squeezing, sonoporation, optical transfection, protoplast fusion, impalefection, magnetofection, gene gun or particle bombardment), chemical reagents (e.g. calcium phosphate, highly branched organic compounds or cationic polymers) or cationic lipids (e.g. lipofection). Many transfection methods require the contact of solutions of plasmid DNA to the cells, which are then grown.

The term "promoter" refers to a sequence that drives gene expression. In order to drive a high level of expression, it may be beneficial to use a high efficiency promoter, such as a non-retroviral, high efficiency promoter. Examples of suitable promoters may include a promoter such as the human cytomegalovirus (CMV) immediate early promoter, spleen focus-forming virus (SFFV) promoter, Rous sarcoma virus (RSV) promoter, or human elongation factor 1-alpha (pEF) promoter.

The term "polyA signal" refers to a polyadenylation signal sequence, for example placed 3' of a transgene, which enables host factors to add a polyadenosine (polyA) tail to the end of the nascent mRNA during transcription. The polyA tail is a stretch of up to 300 adenosine ribonucleotides which protects mRNA from enzymatic degradation and also aids in translation. Accordingly, the nucleic acid vectors of the present invention may include a polyA signal sequence such as the human beta globin or rabbit beta globin polyA signals, the simian virus 40 (SV40) early or late polyA signals, the human insulin polyA signal, or the bovine growth hormone polyA signal. In one embodiment, the polyA signal sequence is the human beta globin polyA signal.

The term "intron sequence" refers to a nucleotide sequence which is removed from the final gene product by RNA splicing. The use of an intron downstream of the enhancer/promoter region and upstream of the cDNA insert has been shown to increase the level of gene expression. The increase in expression depends on the particular cDNA insert. Accordingly, the nucleic acid vector of the present invention may include introns such as human beta globin intron, rabbit beta globin intron II or a chimeric human beta globin-immunoglobulin intron. In one embodiment, the intron is a human beta globin intron and/or a rabbit beta globin intron II.

The term "packaging cell line" refers to a cell line which is capable of expressing gag and pol protein and envelope glycoprotein genes. Alternatively, the term "producer cell line" refers to a packaging cell line which is also capable of expressing a transfer vector containing a transgene of interest.

The term "transiently transfected" refers to transfected cells where the target nucleic acids (i.e. retroviral genes) are not permanently incorporated into the cellular genome. Therefore, the effects of the nucleic acids within the cell last only a short amount of time.

Nucleic Acid Vectors

According to one aspect of the invention, there is provided a nucleic acid vector comprising a non-mammalian origin of replication and the ability to hold at least 25 kilobases (kb) of DNA, characterized in that said nucleic acid vector comprises retroviral nucleic acid sequences encoding:

gag and pol proteins, and an env protein or a functional substitute thereof.

In particular, each of the retroviral nucleic acid sequences may be arranged as individual expression constructs within the nucleic acid vector.

The present inventors have found that nucleic acid vectors described herein can be used to generate retroviral vector particles which ameliorate previous difficulties associated with retroviral vector production methods. For example, by including all of the essential retroviral genes in the nucleic acid vector, the retroviral genes can then be introduced into a mammalian host cell in one single step. Therefore, the use of a nucleic acid vector, as proposed herein, allows for fast vector production and reduces the amount of material required for retroviral vector production.

In one embodiment, the nucleic acid vector additionally comprises nucleic acid sequences which encode the RNA genome of a retroviral vector particle. It will be understood that the RNA genome of the retroviral vector particle is usually included on the "transfer vector" used in transient transfection methods. The transfer vector plasmid generally contains a promoter (such as CMV), the 3' LTR (which may or may not be a self-inactivating (i.e. SIN) 3'-LTR), the 5' LTR (which may or may not contain the U5 region), the encapsidation sequence (ψ) and potentially the transgene linked to a promoter.

In one embodiment, multiple copies of the RNA genome of the retroviral vector particle (i.e. the transfer vector) are included in the nucleic acid vector. Multiple copies of the transfer vector are expected to result in higher viral vector titre. For example, the nucleic acid vector may include two or more, such as three, four, five, six, seven, eight, nine or ten or more copies of the RNA genome of the retroviral vector particle (i.e. the transfer vector).

In one embodiment, the nucleic acid vector contains one or a plurality of recombination site(s). The recombinase enzyme catalyses the recombination reaction between two recombination sites.

Many types of site-specific recombination systems are known in the art, and any suitable recombination system may be used in the present invention. For example, in one embodiment the recombination site(s) are selected or derived from the int/att system of lambda phage, the Cre/lox system of bacteriophage P1, the FLP/FRT system of yeast, the Gin/gix recombinase system of phage Mu, the Cin recombinase system, the Pin recombinase system of *E. coli* and the R/RS system of the pSR1 plasmid, or any combination thereof. In a further embodiment, the recombination site is an att site (e.g. from lambda phage), wherein the att site permits site-directed integration in the presence of a lambda integrase. It will be understood that the reference to "lambda integrase" includes references to mutant integrases which are still compatible with the int/att system, for example the modified lambda integrases described in WO 2002/097059.

In one embodiment, the nucleic acid vector is selected from: a bacterial artificial chromosome (BAC), a yeast artificial chromosome (YAC), a P1-derived artificial chromosome (PAC), fosmid or a cosmid. In a preferred embodiment, the nucleic acid vector is a bacterial artificial chromosome (BAC).

Bacterial Artificial Chromosomes

According to one aspect of the invention, there is provided a bacterial artificial chromosome (BAC), characterized in that said BAC comprises retroviral nucleic acid sequences encoding:
gag and pol proteins, and
an env protein or a functional substitute thereof
wherein each of the retroviral nucleic acid sequences are arranged as individual expression constructs within the BAC.

The term "bacterial artificial chromosome" or "BAC" refers to a DNA construct derived from bacterial plasmids which is able to hold a large insert of exogenous DNA. They can usually hold a maximum DNA insert of approximately 350 kb. BACs were developed from the well characterised bacterial functional fertility plasmid (F-plasmid) which contains partition genes that promote the even distribution of plasmids after bacterial cell division. This allows the BACs to be stably replicated and segregated alongside endogenous bacterial genomes (such as *E. coli*). The BAC usually contains at least one copy of an origin of replication (such as the oriS or oriV gene), the repE gene (for plasmid replication and regulation of copy number) and partitioning genes (such as sopA, sopB, parA, parB and/or parC) which ensures stable maintenance of the BAC in bacterial cells. BACs are naturally circular and supercoiled which makes them easier to recover than linear artificial chromosomes, such as YACs. They can also be introduced into bacterial host cells relatively easily, using simple methods such as electroporation.

In one embodiment, the bacterial artificial chromosome comprises an oriS gene. In one embodiment, the bacterial artificial chromosome comprises a repE gene. In one embodiment, the bacterial artificial chromosome comprises partitioning genes. In a further embodiment, the partitioning genes are selected from sopA, sopB, parA, parB and/or parC. In a yet further embodiment, the bacterial artificial chromosome comprises a sopA and sopB gene.

BAC for use in the present invention may be obtained from commercial sources, for example the pSMART BAC from LUCIGEN™ (see Genome Accession No. EU101022.1 for the full back bone sequence). This BAC contains the L-arabinose "copy-up" system which also contains the oriV medium-copy origin of replication, which is active only in the presence of the TrfA replication protein. The gene for TrfA may be incorporated into the genome of bacterial host cells under control of the L-arabinose inducible promoter araC-P$_{BAD}$ (see Wild et al. (2002) *Genome Res.* 12(9): 1434-1444). Addition of L-arabinose induces expression of TrfA, which activates oriV, causing the plasmid to replicate to up to 50 copies per cell.

Yeast Artificial Chromosomes

The term "yeast artificial chromosome" or "YAC" refers to chromosomes in which yeast DNA is incorporated into bacterial plasmids. They contain an autonomous replication sequence (ARS) (i.e. an origin of replication), a centromere and telomeres. Unlike BACs, the YAC is linear and therefore contains yeast telomeres at each end of the chromosome to protect the ends from degradation as it is passed onto host cell progeny. YACs can hold a range of DNA insert sizes; anything from 100-2000 kb.

P1-Derived Artificial Chromosomes

The term "P1-derived artificial chromosome" or "PAC" refers to DNA constructs derived from the DNA of the P1-bacteriophage and bacterial F-plasmid. They can usually hold a maximum DNA insert of approximately 100-300 kb and are used as cloning vectors in *E. coli*. PACs have similar advantages as BACs, such as being easy to purify and introduce into bacterial host cells.

Cosmids and Fosmids

The term "cosmid" refers to DNA constructs derived from bacterial plasmids which additionally contain cos sites derived from bacteriophage lambda. Cosmids generally contain a bacterial origin of replication (such as oriV), a selection marker, a cloning site and at least one cos site. Cosmids can usually accept a maximum DNA insert of 40-45 kb. Cosmids have been shown to be more efficient at infecting *E. coli* cells than standard bacterial plasmids. The term "fosmids" refers to non-mammalian nucleic acid vectors which are similar to cosmids, except that they are based on the bacterial F-plasmid. In particular, they use the F-plasmid origin of replication and partitioning mechanisms to allow cloning of large DNA fragments. Fosmids can usually accept a maximum DNA insert of 40 kb.

Retroviruses

Retroviruses are a family of viruses which contain a pseudo-diploid single-stranded RNA genome. They encode a reverse transcriptase which produces DNA from the RNA genome which can then be inserted into the host cell DNA. The invention described herein may be used to produce replication defective retroviral vector particles. The retroviral vector particle of the present invention may be selected from or derived from any suitable retrovirus.

In one embodiment, the retroviral vector particle is derived from, or selected from, a lentivirus, alpha-retrovirus, gamma-retrovirus or foamy-retrovirus, such as a lentivirus or gamma-retrovirus, in particular a lentivirus. In a further embodiment, the retroviral vector particle is a lentivirus selected from the group consisting of HIV-1, HIV-2, SIV, FIV, EIAV and Visna. Lentiviruses are able to infect non-dividing (i.e. quiescent) cells which makes them attractive retroviral vectors for gene therapy. In a yet further embodiment, the retroviral vector particle is HIV-1 or is derived from HIV-1. The genomic structure of some retroviruses may be found in the art. For example, details on HIV-1 may be found from the NCBI Genbank (Genome Accession No. AF033819). HIV-1 is one of the best understood retroviruses and is therefore often used as a retroviral vector.

Retroviral Genes

The nucleic acid sequences common to all retroviruses may be explained in more detail, as follows:

Long Terminal Repeats (LTRs): The basic structure of a retrovirus genome comprises a 5'-LTR and a 3'-LTR, between or within which are located the genes required for retroviral production. The LTRs are required for retroviral integration and transcription. They can also act as promoter sequences to control the expression of the retroviral genes (i.e. they are cis-acting genes). The LTRs are composed of three sub-regions designated U3, R, U5: U3 is derived from the sequence unique to the 3' end of the RNA; R is derived from a sequence repeated at both ends of the RNA; and U5 is derived from the sequence unique to the 5' end of the RNA. Therefore, in one embodiment, the nucleic acid vector additionally comprises a 5'- and 3'-LTR. In a further embodiment, the U5 region of the 5' LTR can be deleted and replaced with a non-HIV-1 polyA tail (see Hanawa et al. (2002) *Mol. Ther.* 5(3): 242-51).

In order to address safety concerns relating to the generation of replication-competent virus, a self-inactivating (SIN) vector has been developed by deleting a section in the U3 region of the 3' LTR, which includes the TATA box and binding sites for transcription factors Sp1 and NF-κB (see Miyoshi et al. (1998) *J. Virol.* 72(10):8150-7). The deletion is transferred to the 5' LTR after reverse transcription and integration in infected cells, which results in the transcriptional inactivation of the LTR. This is known as a self-inactivating lentiviral-based vector system which may be included in the present invention.

ψ: Encapsidation of the retroviral RNAs occurs by virtue of a ψ (psi) sequence located at the 5' end of the retroviral genome. It is also well known in the art that sequences downstream of the psi sequence and extending into the gag coding region are involved in efficient retroviral vector production (see Cui et al. (1999) *J. Virol.* 73(7): 6171-6176). In one embodiment, the nucleic acid vector additionally comprises a ψ (psi) sequence.

Primer Binding Site (PBS): The retroviral genome contains a PBS which is present after the U5 region of the 5'-LTR. This site binds to the tRNA primer required for initiation of reverse transcription. In one embodiment, the nucleic acid vector additionally comprises a PBS sequence.

PPT: Retroviral genomes contain short stretches of purines, called polypurine tracts (PPTs), near the 3' end of the retroviral genome. These PPTs function as RNA primers for plus-strand DNA synthesis during reverse transcription. Complex retroviruses (such as HIV-1) contain a second, more centrally located PPT (i.e. a central polypurine tract (cPPT)) that provides a second site for initiation of DNA synthesis. Retroviral vectors encoding a cPPT have been shown to have enhanced transduction and transgene expression (see Barry et al. (2001) *Hum. Gene Ther.* 12(9):1103-8). In one embodiment, the nucleic acid vector additionally comprises a 3'-PPT sequence and/or a cPPT sequence.

The genomic structure of the non-coding regions described above are well known to a person skilled in the art. For example, details on the genomic structure of the non-coding regions in HIV-1 may be found from the NCBI Genbank with Genome Accession No. AF033819, or for HIV-1 HXB2 (a commonly used HIV-1 reference strain) with Genome Accession No. K03455. In one embodiment, the non-coding regions are derived from the sequences available at Genome Accession No. K03455, for example from base pairs 454-1126 (for R-U5-PBS-Gag), 7622-8479 (for RRE) or 7769-8146 (for RRE), 4781-4898 (for cPPT), 9015-9120 & 9521-9719 (for dNEF-PPT-sinU3-R-U5).

Gag/Pol:

The expression of gag and pol genes relies on a translational frameshift between gag and gagpol. Both are polyproteins which are cleaved during maturation. The major structural matrix, capsid, and nucleocapsid proteins of the retroviral vector are encoded by gag. The pol gene codes for the retroviral enzymes: i) reverse transcriptase, essential for reverse transcription of the retroviral RNA genome to double stranded DNA, ii) integrase, which enables the integration of the retroviral DNA genome into a host cell chromosome, and iii) protease, that cleaves the synthesized polyprotein in order to produce the mature and functional proteins of the retrovirus. In one embodiment, the retroviral nucleic acid sequence encoding the gag and pol proteins is derived from the HIV-1 HXB2 sequence, which is available at Genome Accession No. K03455, for example from base pairs 790-5105.

Env:

The env ("envelope") gene codes for the surface and transmembrane components of the retroviral envelope (e.g. glycoproteins gp120 and gp41 of HIV-1) and is involved in retroviral-cell membrane fusion. In order to broaden the retroviral vector's tissue tropism, the retroviral vectors described herein may be pseudotyped with an envelope protein from another virus. Pseudotyping refers to the process whereby the host cell range of retroviral vectors, including lentiviral vectors, can be expanded or altered by changing the glycoproteins (GPs) on the retroviral vector particles (e.g. by using GPs obtained from or derived from other enveloped viruses or using synthetic/artificial GPs). The most commonly used glycoprotein for pseudotyping retroviral vectors is the Vesicular stomatitis virus GP (VSVg), due to its broad tropism and high vector particle stability. However, it will be understood by the skilled person that other glycoproteins may be used for pseudotyping (see Cronin et al. (2005) *Curr. Gene Ther.* 5(4):387-398, herein incorporated by reference in its entirety). The choice of virus used for pseudotyping may also depend on the type of cell and/or organ to be targeted because some pseudotypes have been shown to have tissue-type preferences.

In one embodiment, the env protein or a functional substitute thereof is obtained from or derived from a virus selected from a Vesiculovirus (e.g. Vesicular stomatitis virus), Lyssavirus (e.g. Rabies virus, Mokola virus), Arenavirus (e.g. Lymphocytic choriomeningitis virus (LCMV)), Alphavirus (e.g. Ross River virus (RRV), Sindbis virus, Semliki Forest virus (SFV), Venezuelan equine encephalitis virus), Filovirus (e.g. Ebola virus Reston, Ebola virus Zaire, Lassa virus), Alpharetrovirus (e.g. Avian leukosis virus (ALV)), Betaretrovirus (e.g. Jaagsiekte sheep retrovirus (JSRV)), Gammaretrovirus (e.g. Moloney Murine leukaemia virus (MLV), Gibbon ape leukaemia virus (GALV), Feline endogenous retrovirus (RD114)), Deltaretrovirus (e.g. Human T-lymphotrophic virus 1 (HTLV-1)), Spumavirus (e.g. Human foamy virus), Lentivirus (e.g. Maedi-visna virus (MVV)), Coronavirus (e.g. SARS-CoV), Respirovirus (e.g. Sendai virus, Respiratory syncytia virus (RSV)), Hepacivirus (e.g. Hepatitis C virus (HCV)), Influenzavirus (e.g. Influenza virus A) and Nucleopolyhedrovirus (e.g. *Autographa californica* multiple nucleopolyhedrovirus (AcMNPV)). In a further embodiment, the env protein or a functional substitute thereof is obtained from or derived from Vesicular stomatitis virus. In this embodiment, the Vesicular stomatitis virus glycoprotein (VSVg) protein may be used which enables the retroviral particles to infect a broader host cell range and eliminates the chances of recombination to produce wild-type envelope proteins. In a further embodiment, the retroviral nucleic acid sequence encoding the env protein or a functional substitute thereof, is derived from the sequence available at Genome Accession No. J02428.1, for example from base pairs 3071 to 4720.

The structural genes described herein are common to all retroviruses. Further auxiliary genes may be found in different types of retrovirus. For example, lentiviruses, such as HIV-1, contain six further auxiliary genes known as rev, vif, vpu, vpr, nef and tat. Other retroviruses may have auxiliary genes which are analogous to the genes described herein, however they may not have always been given the same name as in the literature. References such as Tomonaga and Mikami (1996) *J. Gen. Virol.* 77(Pt 8):1611-1621 describe various retrovirus auxiliary genes.

Rev: The auxiliary gene rev ("regulator of virion") encodes an accessory protein which binds to the Rev Response element (RRE) and facilitates the export of retroviral transcripts. The gene's protein product allows fragments of retroviral mRNA that contain the Rev Responsive element (RRE) to be exported from the nucleus to the cytoplasm. The RRE sequence is predicted to form a complex folded structure. This particular role of rev reflects a tight coupling of the splicing and nuclear export steps. In one embodiment, nucleic acid vector comprises an RRE sequence. In a further embodiment, the RRE sequence is derived from HIV-1 HXB2 sequence, which is available at Genome Accession No. K03455, for example from base pairs 7622 to 8479, or 7769 to 8146, in particular base pairs 7622 to 8479.

Rev binds to RRE and facilitates the export of singly spliced (env, vif, vpr and vpu) or non-spliced (gag, pol and genomic RNA) viral transcripts, thus leading to downstream events like gene translation and packaging (see Suhasini and Reddy (2009) *Curr. HIV Res.* 7(1): 91-100). In one embodiment, the nucleic acid vector additionally comprises the auxiliary gene rev or an analogous gene thereto (i.e. from other retroviruses or a functionally analogous system). Inclusion of the rev gene ensures efficient export of RNA transcripts of the retroviral vector genome from the nucleus to the cytoplasm, especially if an RRE element is also included on the transcript to be transported. In a further embodiment, the rev gene comprises at least 60% sequence identity, such as at least 70% sequence identity to base pairs 970 to 1320 of Genome Accession No. M11840 (i.e. HIV-1 clone 12 cDNA, the HIVPCV12 locus). In an alternative embodiment, the rev gene comprises at least 60% sequence identity, such as at least 70%, 80%, 90% or 100% sequence identity to base pairs 5970 to 6040 and 8379 to 8653 of Genome Accession No. K03455.1 (i.e. Human immunodeficiency virus type 1, HXB2).

Auxiliary genes are thought to play a role in retroviral replication and pathogenesis, therefore many current viral vector production systems do not include some of these genes. The exception is rev which is usually present or a system analogous to the rev/RRE system is potentially used. Therefore, in one embodiment, the nucleic acid sequences encoding one or more of the auxiliary genes vpr, vif, vpu, tat and nef, or analogous auxiliary genes, are disrupted such that said auxiliary genes are removed from the RNA genome of the retroviral vector particle or are incapable of encoding functional auxiliary proteins. In a further embodiment, at least two or more, three or more, four or more, or all of the auxiliary genes vpr, vif, vpu, tat and nef, or analogous auxiliary genes, are disrupted such that said auxiliary genes are removed from the RNA genome of the retroviral vector particle or are incapable of encoding functional auxiliary proteins. Removal of the functional auxiliary gene may not require removal of the whole gene; removal of a part of the gene or disruption of the gene will be sufficient.

It will be understood that the nucleic acid sequences encoding the replication defective retroviral vector particle may be the same as, or derived from, the wild-type genes of the retrovirus upon which the retroviral vector particle is based, i.e. the sequences may be genetically or otherwise altered versions of sequences contained in the wild-type virus. Therefore, the retroviral genes incorporated into the nucleic acid vectors or host cell genomes, may also refer to codon-optimised versions of the wild-type genes.

Additional Components

The nucleic acid vectors of the invention may comprise further additional components. These additional features may be used, for example, to help stabilize transcripts for translation, increase the level of gene expression, and turn on/off gene transcription.

The retroviral vector particles produced by the invention may be used in methods of gene therapy. Therefore, in one embodiment, the nucleic acid vector additionally comprises one or more transgenes. This transgene may be a therapeutically active gene which encodes a gene product which may be used to treat or ameliorate a target disease. The transgene may encode, for example, an antisense RNA, a ribozyme, a protein (for example a tumour suppressor protein), a toxin, an antigen (which may be used to induce antibodies or helper T-cells or cytotoxic T-cells) or an antibody (such as a single chain antibody). In one embodiment, the transgene encodes beta globin.

Multiple copies of the transfer vector containing the transgene are expected to result in higher retroviral vector titre, therefore in one embodiment, the nucleic acid vector comprises multiple copies of the transgene, such as two or more, in particular three or more, copies of the transgene. In some cases more than one gene product is required to treat a disease, therefore in a further embodiment, the nucleic acid vector additionally comprises two or more, such as three or more, or four or more, different transgenes.

References herein to "transgene" refer to heterologous or foreign DNA which is not present or not sufficiently expressed in the mammalian host cell in which it is introduced. This may include, for example, when a target gene is not expressed correctly in the mammalian host cell, therefore a corrected version of the target gene is introduced as the transgene. Therefore, the transgene may be a gene of potential therapeutic interest. The transgene may have been obtained from another cell type, or another species, or prepared synthetically. Alternatively, the transgene may have been obtained from the host cell, but operably linked to regulatory regions which are different to those present in the native gene. Alternatively, the transgene may be a different allele or variant of a gene present in the host cell.

The aim of gene therapy is to modify the genetic material of living cells for therapeutic purposes, and it involves the insertion of a functional gene into a cell to achieve a therapeutic effect. The retroviral vector produced using the nucleic acid vectors and host cells described herein can be used to transfect target cells and induce the expression of the gene of potential therapeutic interest. The retroviral vector can therefore be used for treatment of a mammalian subject, such as a human subject, suffering from a condition including but not limited to, inherited disorders, cancer, and certain viral infections.

In one embodiment, the nucleic acid vector additionally comprises a transcription regulation element. For example, any of the elements described herein may be operably linked to a promoter so that expression can be controlled. Promoters referred to herein may include known promoters, in whole or in part, which may be constitutively acting or inducible, e.g. in the presence of a regulatory protein. In one embodiment, the nucleic acid vector additionally comprises a high efficiency promoter, such as a CMV promoter. This promoter has the advantage of promoting a high level of expression of the elements encoded on the non-mammalian nucleic acid vector. In a further embodiment, the CMV promoter comprises a sequence derived from the human cytomegalovirus strain AD169. This sequence is available at Genome Accession No. X17403, for example from base pairs 173731 to 174404.

In one embodiment, the nucleic acid vector additionally comprises an insulator, such as a chromatin insulator. The term "insulator" refers to a genetic sequence which blocks the interaction between promoters and enhancers. In a further embodiment, the insulator (such as a chromatin insulator) is present between each of the retroviral nucleic acid sequences. This helps to prevent promoter interference (i.e. where the promoter from one transcription unit impairs expression of an adjacent transcription unit) between adjacent retroviral nucleic acid sequences. It will be understood that if the insulators are present in the nucleic acid vector between each of the retroviral nucleic acid sequences, then these may be arranged as individual expression constructs within the nucleic acid vector. For example, each sequence encoding the retroviral nucleic acid sequences has its own promoter and/or an intron and/or polyA signal. In one embodiment, the chromatin insulator has at least 90% sequence identity, for example at least 95% sequence identity, to the chicken (*Gallus gallus*) HS4 insulator sequence (for example see Genome Accession No. U78775.2, base pairs 1 to 1205).

In one embodiment, the nucleic acid vector additionally comprises a polyA signal. The use of a polyA signal has the advantage of protecting mRNA from enzymatic degradation and aiding in translation. In a further embodiment, the polyA signal is obtained from or derived from SV40, Bovine Growth Hormone and/or Human Beta Globin. In one embodiment, the polyA signal is derived from the SV40 early polyA signal (for example, see Genome Accession No. EF579804.1, base pairs 2668 to 2538 from the minus strand). In one embodiment, the polyA signal is derived from the Human Beta Globin polyA signal (for example, see Genome Accession No. GU324922.1, base pairs 3394 to 4162).

In one embodiment, the nucleic acid vector additionally comprises an intron sequence. The use of an intron downstream of the enhancer/promoter region and upstream of the cDNA insert (i.e. the transgene) is known to increase the level of expression of the insert. In a further embodiment, the intron sequence is a Human Beta Globin Intron or the Rabbit Beta Globin Intron II sequence. In one embodiment, the Human Beta Globin Intron is derived from the sequence available at Genome Accession No. KM504957.1 (for example from base pairs 476 to 1393). In one embodiment, the Rabbit Beta Globin Intron II is derived from the sequence available at Genome Accession No. V00882.1 (for example, from base pairs 718 to 1290).

In one embodiment, the nucleic acid vector additionally comprises a woodchuck hepatitis virus post-transcriptional regulatory element (WPRE). The presence of WPRE has been shown to enhance expression and as such is likely to be beneficial in attaining high levels of expression. In a further embodiment, the WPRE is derived from the sequence available at Genome Accession No. J04514.1 (for example, from base pairs 1093 to 1684).

In one embodiment, the nucleic acid vector additionally comprises an internal ribosome entry site (IRES). An IRES is a structured RNA element that is usually found in the 5'-untranslated region downstream of the 5'-cap (which is required for the assembly of the initiation complex). The IRES is recognized by translation initiation factors, and allows for cap-independent translation. In a further embodiment, the IRES is derived from the Encephalomyocarditis virus (EMCV) genome (for example, see Genome Accession No. KF836387.1, base pairs 151 to 724).

In one embodiment, the nucleic acid vector additionally comprises a Multiple Cloning Site (MCS). An MCS is a short segment of DNA within the nucleic acid vector which contains multiple restriction sites (for example, 10, 15 or 20 sites). These sites usually occur only once within the nucleic acid vector to ensure that the endonuclease only cuts at one site. This allows for the retroviral genes to be easily inserted using the appropriate endonucleases (i.e. restriction enzymes).

It will be understood by a person skilled in the art that the constructs may be arranged in any order within the nucleic acid vector. In an exemplary embodiment, the nucleic acid vector comprises the following insert: a retroviral nucleic acid sequence encoding the gag and pol proteins, a retroviral nucleic acid sequence encoding the env protein or a functional substitute thereof (such as VSVg) and a retroviral nucleic acid sequence encoding the auxiliary gene rev (such as a codon optimised rev sequence) or an analogous gene thereto or a functionally analogous system (i.e., GagPol-Env-Rev-remaining BAC sequence ("BAC bone"); such as: GagPol-(wild-type)VSVg-(codon-optimised)Rev-pSMARTBAC). In a further embodiment, an insulator (such as a chromatin insulator) is present between each of the gagpol, env and rev sequences. In a further embodiment, a promoter is present before each of the gagpol, env and rev sequences. In a yet further embodiment, at least one copy of the transfer vector sequence (i.e. comprising nucleic acid sequences which encode the RNA genome of a retroviral vector particle) is present before the gagpol sequence.

In one embodiment, the nucleic acid vector comprises the following insert: an insulator (such as a chromatin insulator), a promoter (such as a CMV promoter), an intron (such as a human beta globin intron), a retroviral nucleic acid sequence encoding the gag and pol proteins, a retroviral nucleic acid encoding RRE, a polyA signal (such as a human beta globin polyA signal), an insulator (such as a chromatin insulator), a promoter (such as a CMV promoter), an intron (such as a human beta globin intron), a retroviral nucleic acid sequence encoding the env protein or a functional substitute thereof (such as VSVg), a polyA signal (such as a human beta globin polyA signal), an insulator (such as a chromatin insulator), a promoter (such as a CMV promoter), a retroviral nucleic acid sequence encoding the auxiliary gene rev or an analogous gene thereto or a functionally analogous system, a polyA signal (such as a human beta globin polyA signal), an insulator (such as a chromatin insulator), a promoter (such as a CMV promoter), an intron (such as a rabbit beta globin intron), a polyA signal and a multiple cloning site. It will be understood that further sequences may be included with and/or within this insert.

The nucleic acid sequences may be introduced into the nucleic acid vector sequentially. This allows for selection after each integration to ensure that all of the required nucleic acid sequences are successfully integrated into the nucleic acid vector. Alternatively, at least two or more of the nucleic acid sequences are introduced into the nucleic acid vector simultaneously.

It will be understood that the additional genes described herein may be introduced into the nucleic acid vector by standard molecular cloning techniques known in the art, for example using restriction endonucleases and ligation techniques. Furthermore, the nucleic acid vector, in particular BACs, PACs, fosmids and/or cosmids, may be introduced into bacterial host cells (such as *E. coli* cells, in particular the *E. coli* strain DH10B) by standard techniques, such as electroporation.

Uses

According to a further aspect of the invention, there is provided the nucleic acid vector as defined herein for use in a method of producing retroviral vector particles. As described herein, the present invention provides multiple advantages for using the described nucleic acid vectors in transient transfection methods, mainly by reducing the 4 plasmid transfection system into a single nucleic acid vector thereby reducing the amount of material used.

Methods

According to a further aspect of the invention, there is provided a method of producing a replication defective retroviral vector particle, comprising:
 (a) introducing the nucleic acid vector as defined herein into a culture of mammalian host cells; and
 (b) culturing the mammalian host cells under conditions in which the replication defective retroviral vector particle is produced.

The advantage of including all of the retroviral genes on a large nucleic acid vector is that they can be prepared in microbial cells (such as bacterial or yeast cells) first, which are much easier to handle and manipulate, before being introduced into mammalian cells in a single step.

In one embodiment, the host cell is a mammalian cell. In a further embodiment, the mammalian cell is selected from a HEK 293 cell, HEK 6E cell, CHO cell, Jurkat cell, KS62 cell, PerC6 cell, HeLa cell, HOS cell, H9 cell or a derivative or functional equivalent thereof. In a yet further embodiment, the mammalian host cell is a HEK 293 cell, or derived from a HEK 293 cell. Such cells could be adherent cell lines (i.e. they grow in a single layer attached to a surface) or suspension adapted/non-adherent cell lines (i.e. they grow in suspension in a culture medium). In a yet further embodiment, the HEK 293 cell is a HEK 293T cell or a HEK 6E cell. The term "HEK 293 cell" refers to the Human Embryonic Kidney 293 cell line which is commonly used in biotechnology. In particular, HEK 293T cells are commonly used for the production of various retroviral vectors. Other examples of suitable commercially available cell lines include T REX™ (Life Technologies) cell lines.

The host cells transduced using the methods defined herein may be used to produce a high titre of retroviral vector.

References herein to the term "high titre" refer to an effective amount of retroviral vector or particle which is capable of transducing a target cell, such as a patient cell. In one embodiment, a high titre is in excess of $10^6$ TU/ml without concentration (TU=transducing units).

The skilled person will be aware that introducing the nucleic acid vector into the host cell may be performed using suitable methods known in the art, for example, lipid-mediated transfection (lipofection), microinjection, cell (such as microcell) fusion, electroporation, chemical-based transfection methods or microprojectile bombardment. It will be understood that the choice of method to use for introducing the nucleic acid vector can be chosen depending upon the type of mammalian host cell used. In one embodiment, introduction step (a) is performed using lipofection, electroporation or a chemical-based transfection method. In a further embodiment, the nucleic acid vector is introduced into the host cell by lipofection. In an alternative embodiment, the nucleic acid vector is introduced into the host cell by a chemical-based transfection method, such as calcium phosphate treatment. Calcium phosphate treatments are commercially available, for example from Promega.

It will be understood by the skilled person that the conditions used in the method described herein will be dependent upon the host cell used. Typical conditions, for example the culture medium or temperature to be used, are well known in the art (e.g. see Kutner et al. (2009) *Nature Protocols* 4(4); 495-505). In one embodiment, culturing step (b) is performed by incubating the mammalian host cell under humidified conditions. In a further embodiment, the humidified conditions comprise incubating the transfected cells at 37° C. at 5% $CO_2$. In one embodiment, culturing step (b) is performed using a culture medium selected from: Dulbecco's modified Eagle's medium (DMEM) containing 10% (vol/vol) fetal bovine serum (FBS) or serum-free UltraCULTURE™ medium (Lonza, Cat. No. 12-725F) or FreeStyle™ Expression medium (Thermo fisher, Cat. No. 12338 018).

In one embodiment, the method additionally comprises isolating the replication defective retroviral vector particle. For example, in one embodiment the isolating is performed by using a filter. In a further embodiment, the filter is a low-protein binding membrane (e.g. a 0.22 μm low-protein binding membrane or a 0.45 μm low-protein binding membrane), such as polyvinylidene fluoride (PVDF) or polyethersulfone (PES) artificial membranes.

In one embodiment, the replication defective retroviral vector particles are isolated no longer than 72 hours after introduction step (a). In a further embodiment, the replication defective retroviral vector particles are isolated between 48 and 72 hours after introduction step (a), for example at 48, 49, 50, 51, 52, 53, 54, 55, 56, 57, 58, 59, 60, 61, 62, 63, 64, 65, 66, 67, 68, 69, 70, 71 or 72 hours.

Once isolated, the retroviral vector particles may be concentrated for in vivo applications. Concentration methods include, for example, ultracentrifugation, precipitation or anion exchange chromatography. Ultracentrifugation is useful as a rapid method for retroviral vector concentration at a small scale. Alternatively, anion exchange chromatography (for example using Mustang Q anion exchange membrane cartridges) or precipitation (for example using PEG 6000) are particularly useful for processing large volumes of lentiviral vector supernatants.

According to a further aspect of the invention, there is provided a replication defective retroviral vector particle obtained by the method defined herein.

The invention will now be described in further detail with reference to the following, non-limiting Examples.

EXAMPLES

Example 1: Construct Guide

Figure 1:
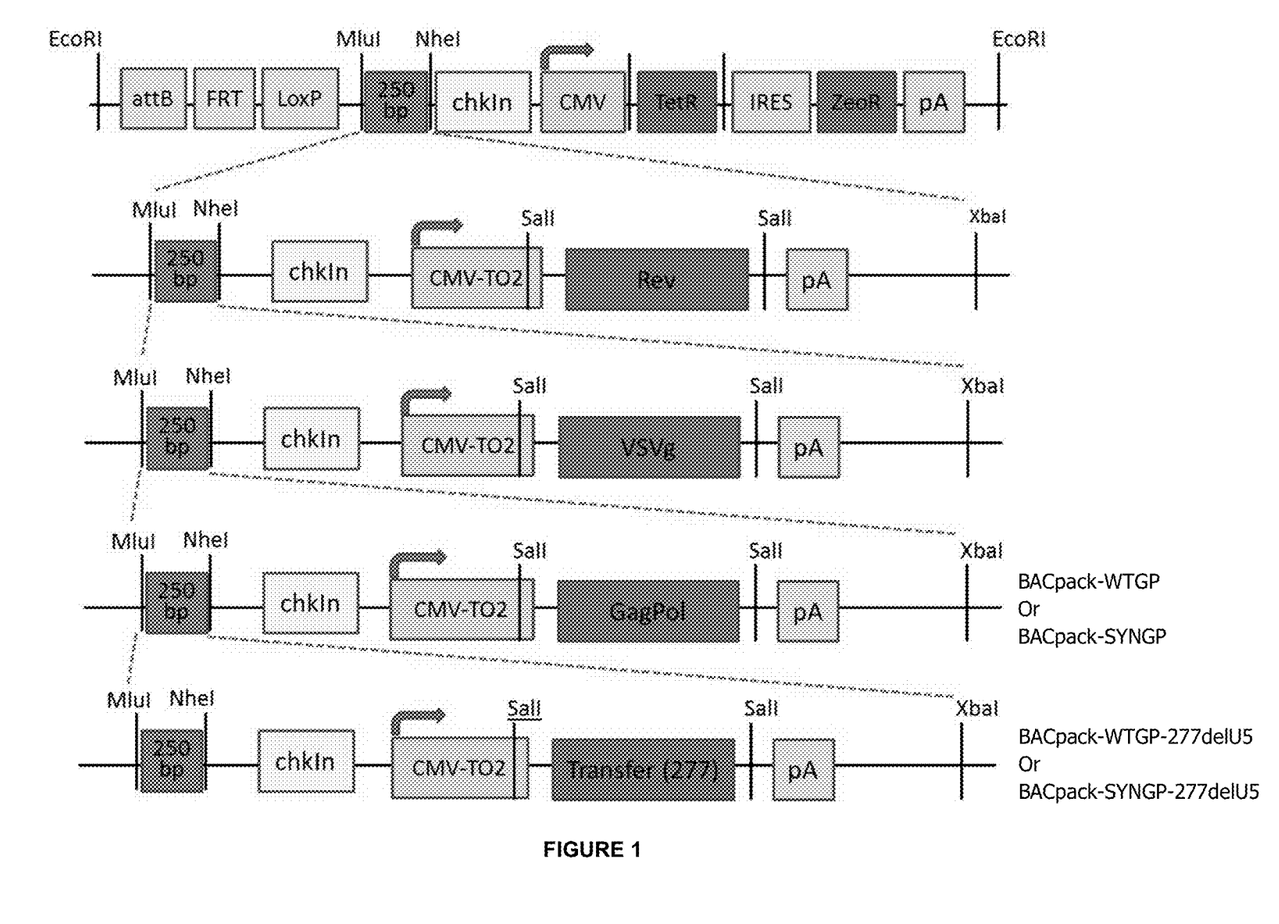
FIG. 1: A stepwise guide to the construction of BACpack-WTGP-277deIU5 and BACpack-SYNGP-277deIU5.

FIG. 1 shows a stepwise guide to the construction of BACpack-WTGP-277deIU5 and BACpack-SYNGP-277deIU5. Owing to the compatible ends of an XbaI and NheI digest, the lentiviral packaging genes were progressively loaded into the pSmart BAC vector. At the point of GagPol addition, 2 constructs were made containing either Wild type GagPol (WTGP) or a codon optimised GagPol (SYNGP). These were given the nomenclature of BACpack-WTGP and of BACpack-SYNGP respectively. The transfer vector was then loaded onto both of these constructs and so generating BACpackWTGP-277deIU5 and BACpackSYNGP-277deIU5.

Example 2: Proof of Principle Experiment Using BAC Construct $10^6$ HEK293T cells were seeded in a 6 well plate. The following day, the adhered cells were transfected using PEI to manufacturer's instruction. Cells were either transfected with a total 4 μg of Wild Type (WT) lentiviral packaging constructs consisting of pMDL.gp (GagPol), pMD.G (VSVg), pK-Rev (Rev) and pCCL.277 (GFP Transfer vector) or 2 μg BACpack (a single BAC construct containing GagPol, VSVg and Rev) plus 2 μg of the eGFP transfer vector on a separate plasmid.

48 hours post transfection, the supernatant was harvested, filtered through a 0.22 μm filter and stored at −80° C. for a minimum of 4 hours. HEK293T cells were seeded for transduction at $10^5$ cells per well in a 24 well plate. The following day viral supernatant was applied to the cells in serial dilutions with Polybrene at a final concentration of 8 μg/ml. 3 days post transduction the cells were harvested by trypsin treatment and analysed for GFP by FACS. Viral titre was calculated as Transduction Units (TU)/mL using the following equation:

(*GFP* positive cells/100)×dilution factor×number of cells transduced.

Figure 2:
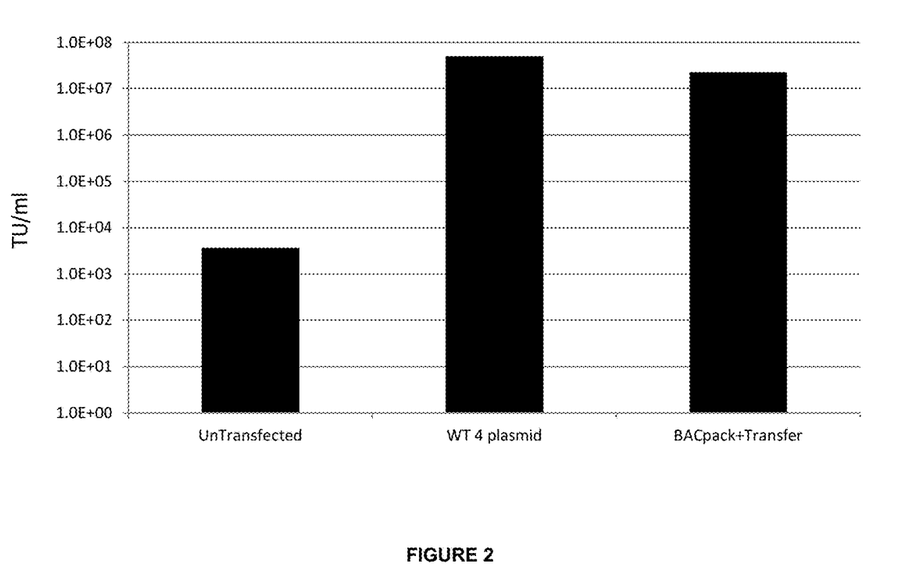

Viral titres are compared on the barchart (FIG. 2). All incubations were carried out at 37° C. and 5% $CO_2$. Media used was DMEM supplemented with FBS to 10% and 1 μg/ml Doxycycline in the BACpack+Transfer sample.

Observations:

In this Example, the ability of the BACpack construct, consisting of GagPol, VSVg and Rev expression cassettes was compared to the standard 3 plasmid packaging system where GagPol, VSVg and Rev are delivered separately. In both cases, the transfer vector was delivered alongside in a separate plasmid in order to complete the essential components for the viral vector.

In this instance, the BACpack plus transfer vector was capable of achieving an unconcentrated supernatant viral titre of $2.2\times10^7$ TU/ml, compared to a titre of $5\times10^7$ TU/ml when using the 4 separate plasmid lentivirus system. Although a lower titre was observed using the BACpack, this assay was performed pre-optimisation and a greater titre may be achieved post-optimisation.

From this proof of principal assay, it can be concluded that the BACpack is capable of packaging of the transfer vector at a viral titre comparable to that of the separate packaging plasmid system in a transient transfection.

Example 3: Transient Transfection of the BACpack in Adherent HEK293T Cells

In order to confirm the ability of the two BACpack-277deIU5 constructs to produce lentiviral vector in a transient transfection system the adherent cell line, HEK293T, routinely used to produce lentiviral vector by transient transfection, were transfected with either the current 4 packaging plasmid system, BACpackWTGP-277deIU5 or BACpackSYNGP-277deIU5. The two BACpack-277deIU5 constructs were either induced to assess whether gene expression could result in lentiviral vector production or left uninduced to test the efficiency of the Tet Repressor system.

Figure 3:
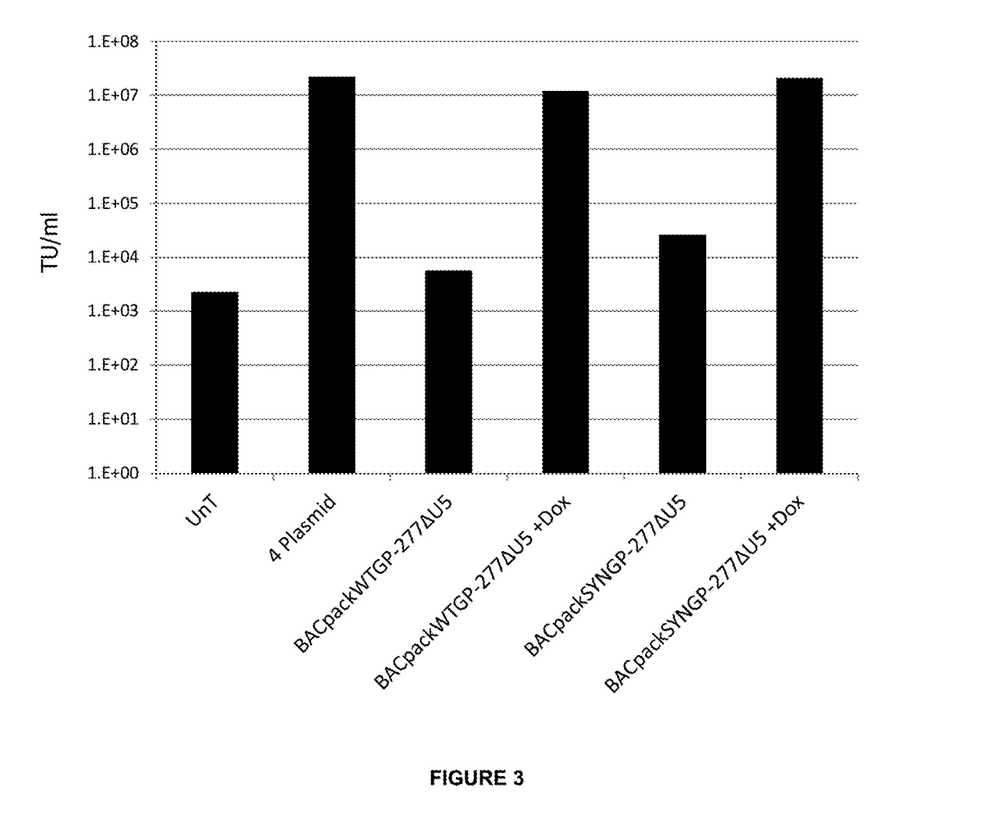

The results in FIG. 3 show the titre in transduction units (TU)/mL, of the lentiviral vector supernatant harvested from each transfection condition. It can be seen from the titration results that cells transfected with either BACpackWTGP-277deIU5 or BACpackSYNGP-277deIU5 and induced with 1 ug/ml Doxycycline (+Dox) produced comparable concentrations of lentiviral vector as the current 4 plasmid system. In addition, the uninduced conditions demonstrated a greatly reduced ability to produce lentiviral vector compared to induced, and although this production was greater than the un-transfected control background, this is not seen to be a disadvantage in a transient system.

These results suggests that the single BAC vector containing all of the packaging genes necessary for lentiviral production could replace the current 4 plasmid system.

It will be understood that the embodiments described herein may be applied to all aspects of the invention. Furthermore, all publications, including but not limited to patents and patent applications, cited in this specification are herein incorporated by reference as though fully set forth.

The invention claimed is:

1. A bacterial artificial chromosome (BAC), characterized in that said BAC comprises retroviral nucleic acid sequences encoding: gag and pol proteins, and an env protein or a functional substitute thereof wherein each of the retroviral nucleic acid sequences are arranged as individual expression constructs within the BAC.

2. The bacterial artificial chromosome of claim 1, which additionally comprises nucleic acid sequences which encode the RNA genome of a retroviral vector particle.

3. The bacterial artificial chromosome of claim 1, which additionally comprises the auxiliary gene rev or an analogous gene thereto or a functionally analogous system.

4. The bacterial artificial chromosome of claim 1, wherein the retroviral nucleic acid sequences are obtained from a retrovirus selected from lentivirus, alpha-retrovirus, gammaretrovirus or foamy-retrovirus.

5. The bacterial artificial chromosome of claim 4, wherein the retroviral nucleic acid sequences are obtained from a lentivirus selected from the group consisting of HIV-1, HIV-2, SIV, FIV, EIAV and Visna.

6. The bacterial artificial chromosome of claim 5, wherein the retroviral nucleic acid sequences are obtained from HIV-1.

7. The bacterial artificial chromosome of claim 1, wherein the env protein or a functional substitute thereof is obtained from Vesicular stomatitis virus.

8. The bacterial artificial chromosome of claim 1, which additionally comprises a transcription regulation element.

9. The bacterial artificial chromosome of claim 8, wherein the transcription regulation element is a CMV promoter.

10. The bacterial artificial chromosome of claim 1, which additionally comprises an insulator.

11. The bacterial artificial chromosome of claim 10, wherein an insulator is present between each of the retroviral nucleic acid sequences.

12. The bacterial artificial chromosome of claim 1, which additionally comprises one or more transgenes.

13. The bacterial artificial chromosome of claim 1, which additionally comprises an Internal Ribosome Entry Site (IRES).

14. The bacterial artificial chromosome of claim 1, which additionally comprises a polyA signal.

15. The bacterial artificial chromosome of claim 1, which additionally comprises an intron sequence.

16. The bacterial artificial chromosome of claim 1, which additionally comprises a Multiple Cloning Site (MCS).

17. A method of producing a replication defective retroviral vector particle, comprising:
(a) introducing into a culture of mammalian host cells, a bacterial artificial chromosome (BAC), characterized in that said BAC comprises retroviral nucleic acid sequences encoding: gag and pol proteins, and an env protein or a functional substitute thereof wherein each of the retroviral nucleic acid sequences are arranged as individual expression constructs within the BAC; and
(b) culturing the mammalian host cells under conditions in which the replication defective retroviral vector particle is produced.

18. The method of claim 17, wherein the mammalian host cell is a HEK 293 cell.

19. The method of claim 17, wherein introduction step (a) is performed using lipofection, electroporation or a chemical-based transfection method, such as calcium phosphate treatment.

20. The method of claim 17, wherein culturing step (b) is performed by incubating the mammalian host cell under humidified conditions.

21. The method of claim 17, additionally comprising isolating the replication defective retroviral vector particle.

22. The method of claim 21, wherein the isolating is performed by using a filter, such as a low-protein binding membrane.

23. The method of claim 21, wherein the replication defective retroviral vector particles are isolated no longer than 72 hours after introduction step (a).

24. The method of claim 23, wherein the replication defective retroviral particles are isolated between 48 and 72 hours after introduction step (a).

* * * * *